United States Patent
Jacobs et al.

(10) Patent No.: US 10,314,528 B2
(45) Date of Patent: Jun. 11, 2019

(54) PATIENT SUPPORT PAD

(71) Applicant: American Sterilizer Company, Mentor, OH (US)

(72) Inventors: Nicholas Jacobs, Chagrin Falls, OH (US); Richard P. Nardo, Highland Heights, OH (US); Christopher D. Labedz, Streetsboro, OH (US); Sohrab Soltani, Charleston, SC (US); Michael Hollopeter, Kirtland, OH (US)

(73) Assignee: American Sterilizer Company, Mentor, OH (US)

( * ) Notice: Subject to any disclaimer, the term of this patent is extended or adjusted under 35 U.S.C. 154(b) by 387 days.

(21) Appl. No.: 15/159,866

(22) Filed: May 20, 2016

(65) Prior Publication Data

US 2017/0332803 A1 Nov. 23, 2017

(51) Int. Cl.
  *A61B 5/00* (2006.01)
  *A47C 27/15* (2006.01)
  *A47C 21/04* (2006.01)
  *A47C 27/00* (2006.01)
  *A61G 7/057* (2006.01)
  (Continued)

(52) U.S. Cl.
  CPC ............ *A61B 5/447* (2013.01); *A47C 21/048* (2013.01); *A47C 27/001* (2013.01); *A47C 27/15* (2013.01); *A61G 7/057* (2013.01); *A61G 13/10* (2013.01); *A61G 13/126* (2013.01); *A61B 2562/02* (2013.01); *A61B 2562/0252* (2013.01); *A61G 7/0573* (2013.01); *A61G 2007/0527* (2013.01); *A61G 2203/34* (2013.01); *A61G 2203/46* (2013.01)

(58) Field of Classification Search
  CPC ..... A47C 21/048; A47C 27/001; A47C 27/15; A61G 13/10; A61G 13/126; A61G 2203/30; A61G 2203/34; A61G 7/05; A61G 7/057; A61G 7/05723; A61G 7/0573; A61G 2007/0527; A61B 5/447; A61B 2562/00; A61B 2562/02; A61B 2562/0252
  See application file for complete search history.

(56) References Cited

U.S. PATENT DOCUMENTS

| 4,584,625 | A | * | 4/1986 | Kellogg | ................. | B25J 13/084 |
|---|---|---|---|---|---|---|
|  |  |  |  |  |  | 361/283.1 |
| 5,571,973 | A | * | 11/1996 | Taylot | ................. | A61B 5/1036 |
|  |  |  |  |  |  | 73/862.046 |

(Continued)

OTHER PUBLICATIONS

BodiTrak Smart Bed (http://www.boditrak.com/products/smartbed.php).

(Continued)

*Primary Examiner* — Nicholas F Polito
*Assistant Examiner* — David R Hare
(74) *Attorney, Agent, or Firm* — Kusner & Jaffe

(57) ABSTRACT

A support pad, including a first cushion layer, a second cushion layer, and a sensing device, is provided. The sensing device is positioned between the first and second cushion layers. The sensing device includes a plurality of sensing elements and a substrate. The substrate includes a plurality of tab portions and a plurality of expandable portions. The sensing elements are respectively mounted to the tab portions. The expandable portions are moveable between contracted and expanded positions in response to pressure applied thereto.

20 Claims, 6 Drawing Sheets

(51) Int. Cl.
*A61G 13/10* (2006.01)
*A61G 13/12* (2006.01)
*A61G 7/05* (2006.01)

(56) References Cited

U.S. PATENT DOCUMENTS

| | | | | |
|---|---|---|---|---|
| 5,606,136 | A * | 2/1997 | Kropp | H03K 17/9645 73/862.045 |
| 7,201,063 | B2 * | 4/2007 | Taylor | A61B 5/103 73/841 |
| 7,469,437 | B2 | 12/2008 | Mikkelsen et al. | 5/740 |
| 8,621,687 | B2 | 1/2014 | Brykalski et al. | 5/421 |
| 8,661,915 | B2 | 3/2014 | Taylor | 73/862.044 |
| 9,333,136 | B2 | 5/2016 | Gibson et al. | A61G 7/05769 |
| 2005/0076715 | A1 * | 4/2005 | Kuklis | A61B 5/11 73/541 |
| 2005/0165284 | A1 * | 7/2005 | Gefen | G06F 19/00 600/300 |
| 2009/0056020 | A1 * | 3/2009 | Caminade | A61B 5/447 5/600 |
| 2009/0070939 | A1 * | 3/2009 | Hann | A61B 5/11 5/652.1 |
| 2011/0263950 | A1 * | 10/2011 | Larson | A61B 5/1113 128/845 |
| 2013/0006151 | A1 | 1/2013 | Main et al. | 600/587 |
| 2014/0059778 | A1 * | 3/2014 | Jalbert | A61B 5/6891 5/690 |
| 2014/0237722 | A1 * | 8/2014 | Gibson | A61G 7/05769 5/600 |
| 2014/0243709 | A1 * | 8/2014 | Gibson | A61B 5/6892 600/587 |
| 2014/0350882 | A1 * | 11/2014 | Everett | G01L 25/00 702/98 |
| 2015/0047646 | A1 * | 2/2015 | Marinkovic | A61H 1/008 128/845 |
| 2016/0015311 | A1 * | 1/2016 | Jiang | A61F 2/80 623/33 |
| 2017/0089775 | A1 * | 3/2017 | Hsu | G01L 1/16 |
| 2017/0172489 | A1 * | 6/2017 | Afentakis | G01D 5/1655 |
| 2017/0172490 | A1 * | 6/2017 | Afentakis | A61B 5/447 |
| 2018/0020841 | A1 * | 1/2018 | Mitsuzuka | A61G 7/05 5/737 |
| 2018/0055252 | A1 * | 3/2018 | Jensen | A47G 9/1081 |

OTHER PUBLICATIONS

Xsensor Pressure Map (http://www.xsensor.com/x3_medical_6).
Sacks, A., "Theoretical prediction of a time-at-pressure curve for avoiding pressure sores," Journal of Rehabilitation Research and Development, Department of Veterans Affairs, vol. 26, No. 3, pp. 27-34.
Linder-Ganz et al., "Mechanical compression-induced pressure sores in rat hindlimb: muscle stiffness, histology, and computational models," Journal of Applied Physiology, vol. 96, pp. 2034-2049, Feb. 6, 2004.
Sprigle et al., "Assessing evidence supporting redistribution of pressure for pressure ulcer prevention: A review," Journal of Rehabilitation Research & Development, U.S. Department of Veterans Affairs, vol. 48, No. 3, pp. 203-214, 2011.
Loerakker et al., "The effects of deformation, ischemia, and reperfusion on the development of muscle damage during prolonged loading," Journal of Applied Physiology, vol. 111, pp. 1168-1177, Jul. 14, 2011.
International Search Report and Written Opinion issued in corresponding International Application No. PCT/US2017/031648 dated Jul. 19, 2017.
Kosiak M., "Etiology of Decubitus Ulcers," Archives of Physical Medicine & Rehabilitation, 1959, 40(2):6269 [PMID: 13618101].
Reswick et al., "Experience at Rancho Los Amigos Hospital with Devices and Techniques to Prevent Pressure Sores," Bed Sore Biomechanics, pp. 301-310, 1976.
Linder-Ganz et al., "Pressure-time cell death threshold for albino rat skeletal muscles as related to pressure sore biomechanics," Journal of Biomechanics, vol. 39, pp. 2725-2732.
Cuddigan, et al., "Pressure Ulcers: Prevalence, Incidence, and Implications for the Future," National Pressure Ulcer Advisory Panel, Washington, DC: NPUAP, 2012.

* cited by examiner

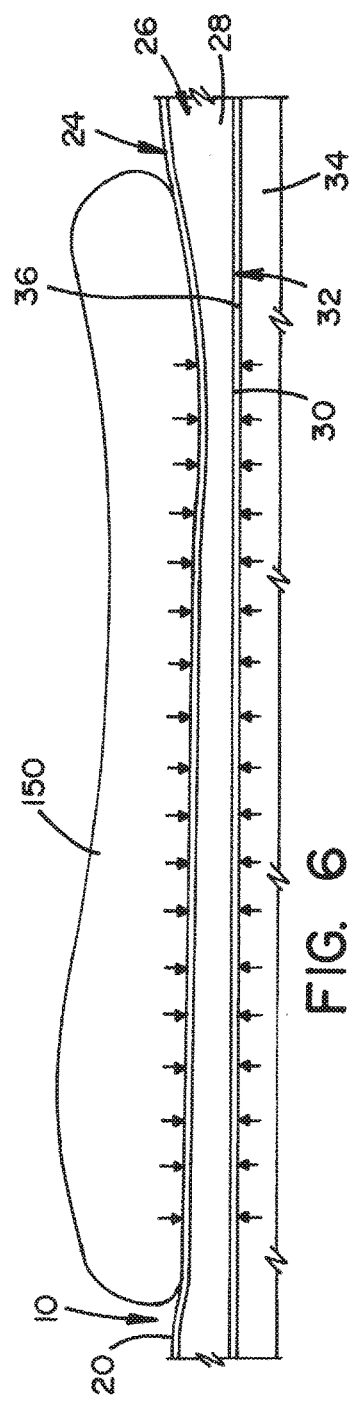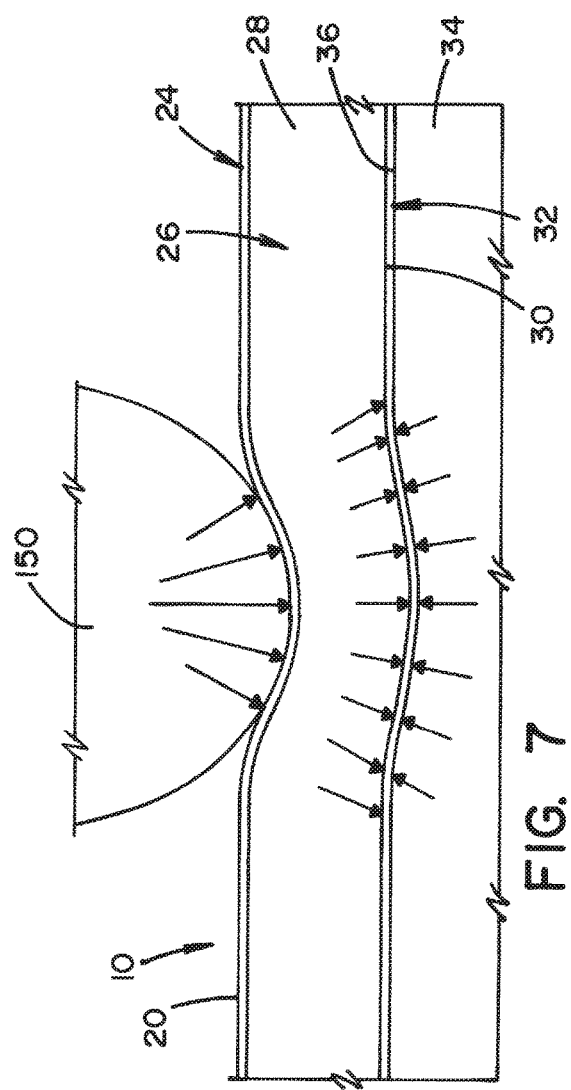

PATIENT SUPPORT PAD

FIELD OF INVENTION

The present invention relates generally to the field of patient support devices, and, more particularly, a support pad having embedded electronic components.

BACKGROUND OF INVENTION

A support pad is typically used to support a patient undergoing a surgical procedure. The patient positioned on the support pad applies a load to the support pad. At least a portion of the load is resisted by the support pad. The resistance of the support pad serves to create an interface pressure at the surface of the support pad on which the patient is positioned. The interface pressure is applied to the patient's tissues contacting the surface of the support pad. Pressure ulcers are more likely to develop in tissues that have been exposed to long periods of elevated interface pressure.

An amount of interface pressure applied to the tissues is generally related to respective loads applied to the support pad and an ability of the support pad to redistribute loads over the surface of the support pad. For example, a rigid support pad may be less likely to effectively redistribute loads therein than a soft support pad due to an inability of a surface of the rigid support pad to envelop the loads. This is at least partially due to the tendency of rigid surfaces to resist an application of force thereto. Thus, a greater peak of interface pressure may be applied to the tissues by the rigid pad than the soft pad.

Pressure sensing devices or other electronic components embedded in a support pad (e.g., temperature sensing, heating or excitation devices) are commonly positioned adjacent to an outer surface of the support pad. However, these electronic components are generally semi-rigid, thereby leading to increases in interface pressure and reduced load redistribution through the support pad.

The present invention provides a support pad with embedded electronic components that overcomes these and other drawbacks of the prior art.

SUMMARY OF INVENTION

In accordance with the present invention, there is provided a support pad. The support pad includes a first cushion layer, a second cushion layer, and a sensing device. The sensing device is positioned between the first and second cushion layers. The sensing device includes a plurality of sensing elements and a substrate. The substrate includes a plurality of tab portions and a plurality of expandable portions. The sensing elements are respectively mounted to the tab portions. The expandable portions are moveable between contracted and expanded positions in response to pressure applied thereto.

In accordance with another embodiment of the present invention, there is provided a support pad. The support pad includes a first cushion layer, a second cushion layer, and an electronic device. The electronic device is positioned between the first and second cushion layers. The electronic device includes a plurality of electronic elements and a substrate. The substrate includes a plurality of tab portions and a plurality of expandable portions. The electronic elements are respectively mounted to the tab portions. The expandable portions are moveable between contracted and expanded positions in response to pressure applied thereto.

In accordance with a further embodiment of the present invention, there is provided a support pad assembly. The support pad assembly includes a first support pad. The first support pad includes a first cushion layer, a second cushion layer, and a sensing device. The sensing device is positioned between the first and second cushion layers. The sensing device includes a plurality of sensing elements and a substrate. The substrate includes a plurality of tab portions and a plurality of expandable portions. The sensing elements are respectively mounted to the tab portions. The expandable portions are moveable between contracted and expanded positions in response to pressure applied thereto.

An advantage of the present invention is the provision of a support pad that enables improved redistribution of loads applied to the support pad.

Another advantage of the present invention is the provision of a support pad including a sensing device that enables accurate sensing of interface pressure for both acute and distributed loads applied to tissues of a patient at a surface of the support pad.

An additional advantage of the present invention is the provision of a support pad including a sensing device designed to reduce interface pressure generated at a surface of the support pad without causing an appreciable difference to interface pressure.

A further advantage of the present invention is the provision of a support pad including electronic components located on a substrate that is flexible, strong, and compatible with printed electronic devices.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 6 is a cross-sectional side view illustrating an example of a support pad according to an embodiment of the present invention to which a distributed load is applied; and FIG. 7 is a cross-sectional side view illustrating an example of a support pad according to an embodiment of the present invention to which an acute load is provided.

DETAILED DESCRIPTION OF INVENTION

The present invention will now be described with reference to a support pad that includes a pressure sensing device.

However, it will be appreciated that the support pad of the present invention may also include other electronic devices, including, but not limited to, temperature sensing, strain sensing, moisture sensing, ultraviolet energy sensing, heating, and excitation devices.

Figure 1:
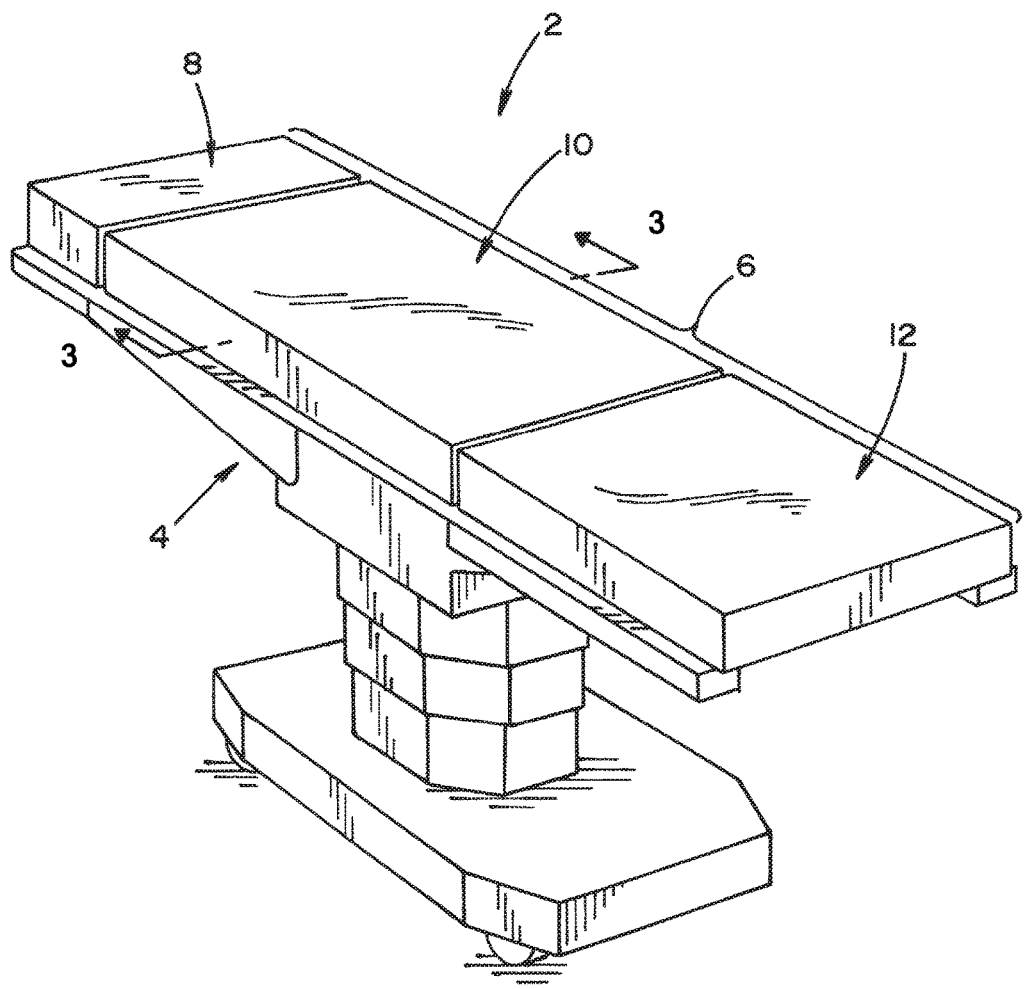
FIG. 1 is a perspective view illustrating a support pad assembly according to an embodiment of the present invention, wherein the support pad assembly is positioned on an example surgical table.

Referring now to the drawings wherein the showings are for the purposes of illustrating embodiments of the invention only and not for the purposes of limiting same, FIG. 1 shows a support pad assembly 6 according to an embodiment of the present invention. Support pad assembly 6 is positioned on a support surface 4 of a surgical table 2 to support and cushion a patient that is situated thereon.

In the illustrated embodiment, support pad assembly 6 is generally comprised of support pads 8, 10, and 12 for respectively supporting and cushioning a head, a torso, and a leg/foot region of a patient.

Support pad assembly 6 is generally comprised of one or more support pads according to patient positioning needs. While support pads 8, 10, and 12 are illustrated as being positioned on support surface 4 of surgical table 2, it will be readily appreciated that support pads 8, 10, and 12 may be used to support and cushion a patient on any suitable support surface known in the art. For example, support pads 8, 10, and 12 may be used in connection with support surfaces of a hospital bed, an examination table, a mattress, a foam pad, a gurney, and the like. In addition, support pads 8, 10, and 12 may be configured to accommodate various patient positions, including, but not limited to, supine, prone, lithotomy, lateral, trendelenberg, reverse trendelenberg, beach chair, and seated positions. Further, in an alternative embodiment, support pad assembly 6 is a single support pad sized to cover an entire area of support surface 4.

Figure 2:
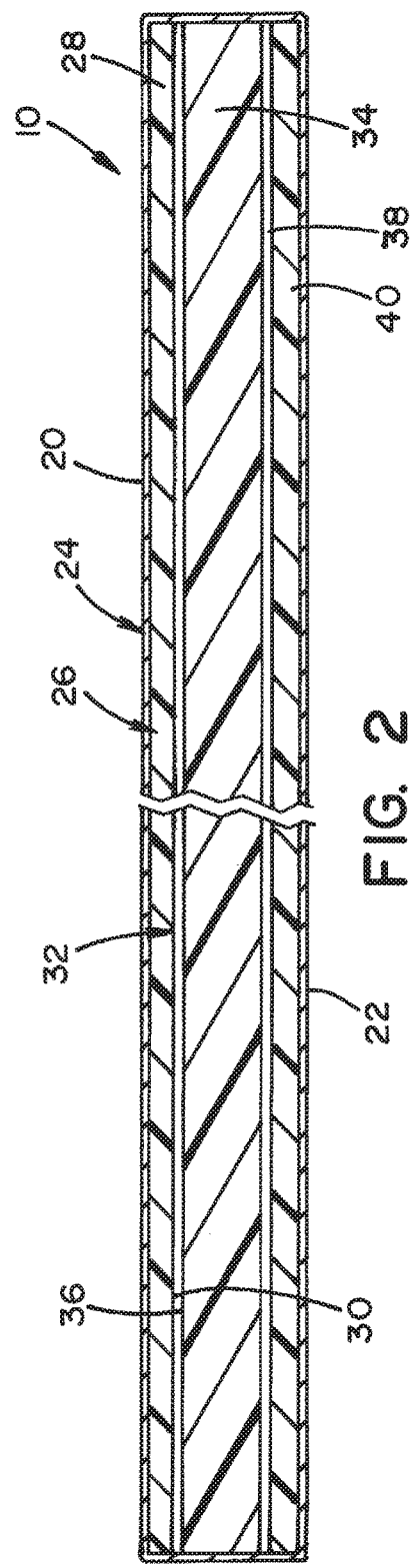
FIG. 2 is a cross-sectional view of a support pad taken along lines 3-3 of FIG. 1 according to an embodiment of the present invention.

FIG. 2 shows a cross-sectional view of support pad 10 taken along lines 3-3 of FIG. 1 according to an embodiment of the present invention. Support pad 10 is generally comprised of a cover 24 and a layer assembly 26, both of which are radiolucent. Cover 24 surrounds and houses layer assembly 26, and also defines top and bottom surfaces 20 and 22 of support pad 10. A patient is positioned on top surface 20. Bottom surface 22 is positioned on a support surface, such as support surface 4. Cover 24 may be comprised of a soft and pliable polymer material that stretches in response to applied pressure, such as, but not limited to, vinyl-based materials. An example thickness of support pad 10 is in a range of about 1.0 inch to about 5.0 inches, but is not limited thereto.

In the illustrated embodiment, layer assembly 26 is generally comprised of, from a bottom to a top thereof, a lower cushion layer 40, a controller unit 38, a middle cushion layer 34, a sensing device 32, and an upper cushion layer 28.

Upper cushion layer 28 is located adjacent to top surface 20 of support pad 10. Upper cushion layer 28 provides tactile isolation of sensing device 32 from top surface 20 of support pad 10. In the illustrated embodiment, upper cushion layer 28 is comprised of a foam material having a thickness in a range of about 0.125 inches to about 0.75 inches and a density in a range of about 2.8 lbs/ft$^3$ to about 5.0 lbs/ft$^3$. Suitable types of foam material for upper cushion layer 28 include, but are not limited to, soft core memory foam, visco-elastic foam, gel-infused foam, slow-recovery foam, latex foam, or other flexible polyurethane foam material. Other suitable materials for upper cushion layer 28 include, but are not limited to, cotton, latex, and polyester.

Figure 3:
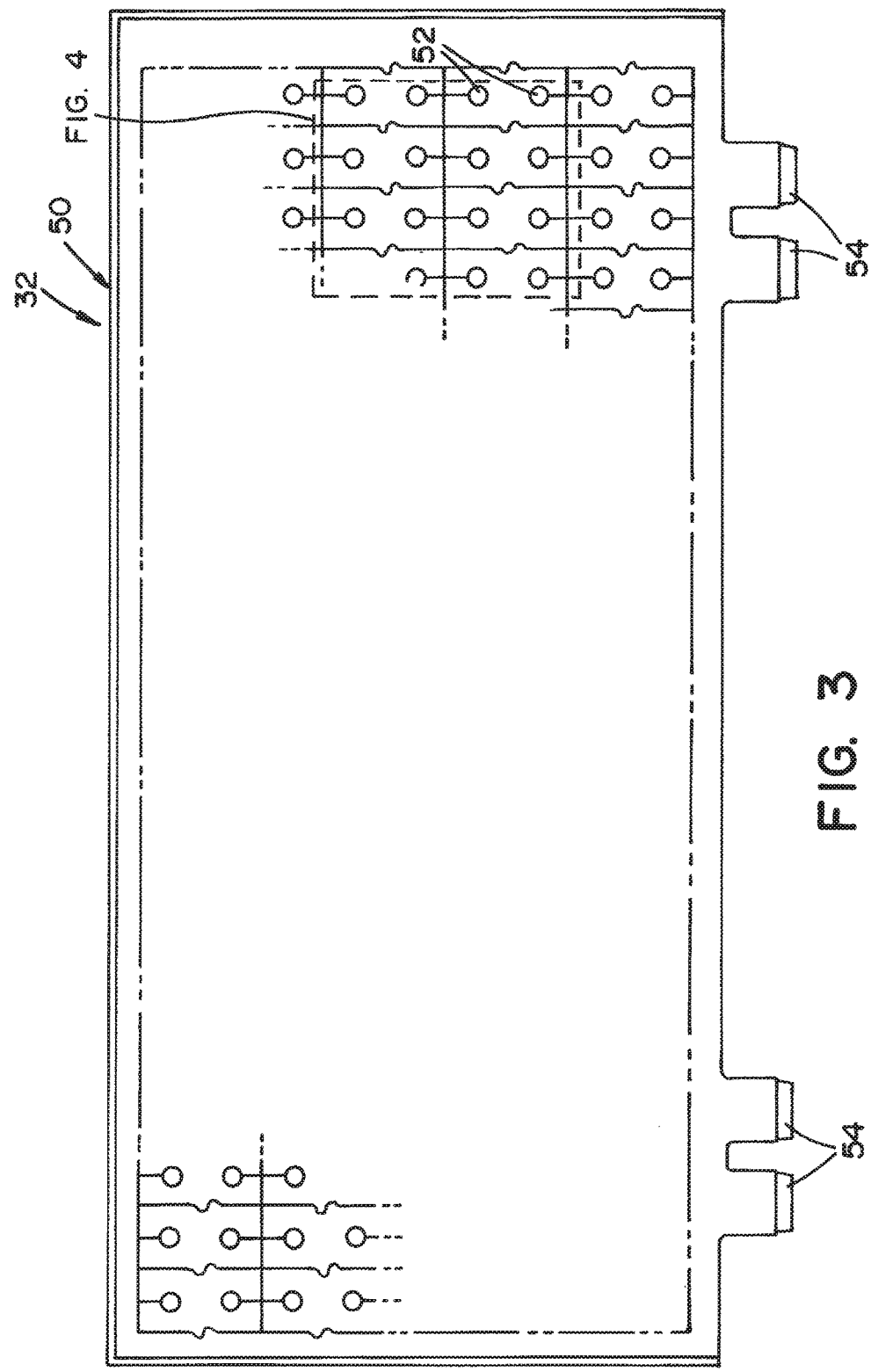
FIG. 3 is a top view of a sensing device of the support pad shown in FIG. 2 according to an embodiment of the present invention.
Figure 4:
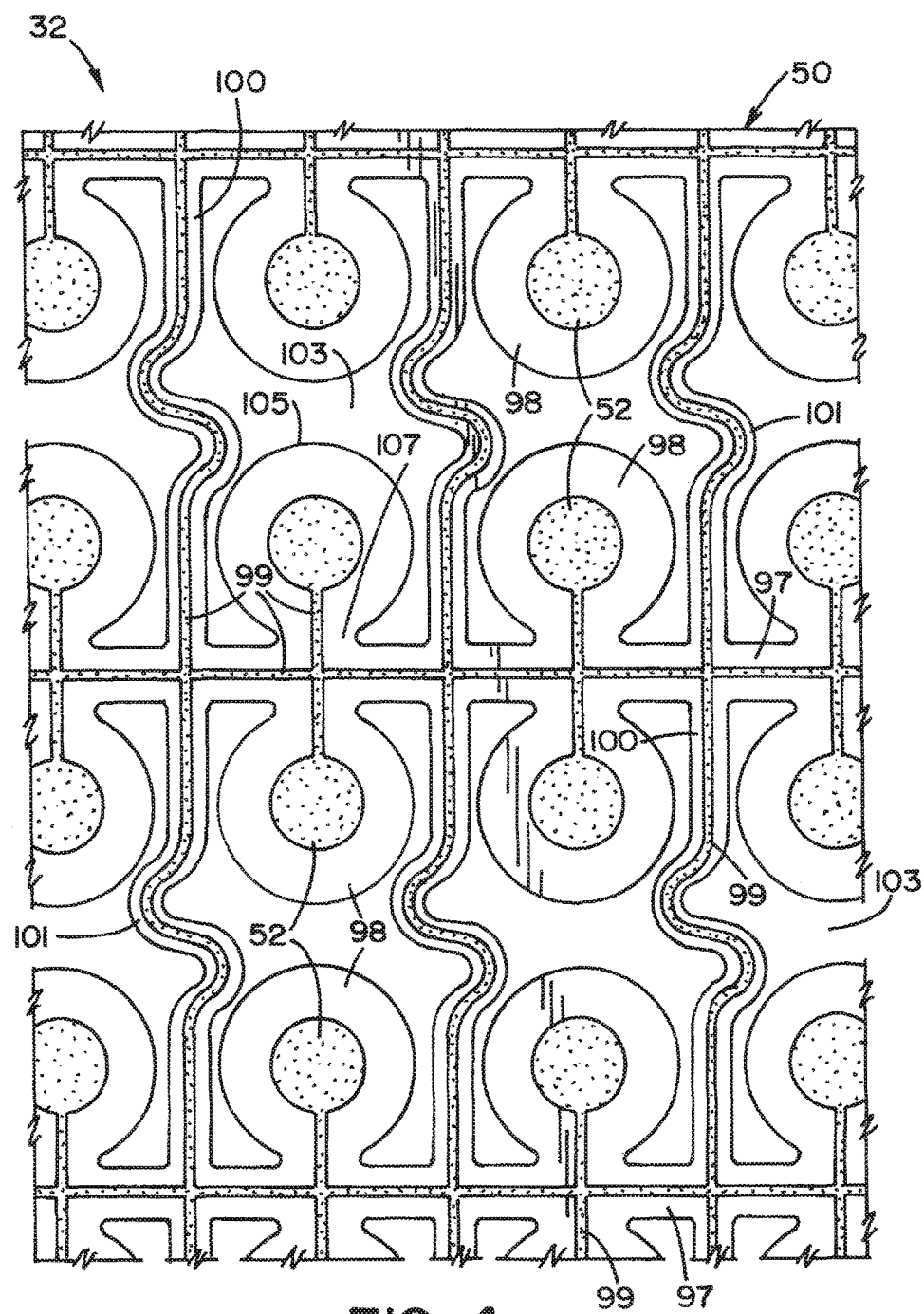
FIG. 4 is an enlarged view of a portion of the sensing device shown in FIG. 3 according to an embodiment of the present invention.

FIG. 3 shows a top view of sensing device 32 of support pad 10 shown in FIG. 2 according to an embodiment of the present invention. FIG. 4 shows an enlarged view of a portion of sensing device 32 shown in FIG. 3 according to an embodiment of the present invention.

Sensing device 32 is positioned between upper and middle cushion layers 28 and 34. A bottom surface 30 of upper cushion layer 28 and a top surface 36 of middle cushion layer 34 are in contact with sensing device 32. Sensing device 32 is generally comprised of a substrate 50, a plurality of sensing elements 52, at least one communication interface 54, and a plurality of conductive trace lines 99.

Sensing elements 52 are configured to sense pressure applied by a load onto cover 24 and transmitted through cover 24 and upper cushion layer 28. In the illustrated embodiment, each sensing element 52 is a load-sensitive resistor sensing cell, or a sensel, but is not limited thereto.

As best seen in FIG. 4, substrate 50 is generally comprised of a plurality of row and column sections 97 and 100 on which conductive trace lines 99 are respectively formed, a plurality of tab portions 98 on which sensing elements 52 are respectively located, and openings 103 defined by row sections 97, column sections 100, and tab portions 98. Conductive trace lines 99 electrically connect sensing elements 52 with communication interfaces 54 located at the edge of sensing device 32.

Each column section 100 includes at least one expandable portion 101 that is biased in a contracted position. Each expandable portion 101 is moveable between contracted and expanded positions and configured to expand in response to a load applied to upper cushion layer 28. Sections of conductive trace lines 99 that are respectively formed on expandable portions 101 expand and contract according to the expansion and contraction of expandable portions 101. Further, each tab portion 98 has a fixed end 107 attached to a row section 97 and a free end 105 extending from the row section 97 into a corresponding opening 103. Each tab portion 98 is free to move and flex within the respective openings 103.

In the illustrated embodiment, sensing device 32 is arranged as a layer of layer assembly 26. However, it will be appreciated that other arrangements of the above-referenced elements of sensing device 32 and substrate 50 may be implemented and will be apparent to those of ordinary skill in the art.

Further, in the illustrated embodiment, substrate 50 serves to provide a matrix of sensing elements 52. However, the structure of substrate 50 and arrangements of sensing elements 52 located on substrate 50 are not limited thereto. Additionally, it is conceivable for row sections 97 to include expandable portions 101 in place of or in addition to expandable portions 101 of column sections 100. Moreover, in the illustrated embodiment, substrate 50 is made of a flexible polymer sheet. Other suitable materials for substrate 50 include, but are not limited to, polyethylene terephthalate (PET), polyimide, and thermoplastic polyurethane.

Referring again to FIG. 2, middle cushion layer 34 is positioned between sensing device 32 and controller unit 38. In the illustrated embodiment, middle cushion layer 34 is a foam layer having a thickness in a range of about 1.0 inch to about 4.0 inches and a density in a range of about 2.5 lbs/ft$^3$ to about 4.0 lbs/ft$^3$. It will be appreciated that middle cushion layer 34 may be split into multiple cushion layers constructed of the same or different materials. For example, middle cushion layer 34 may be formed of cushion materials as described above in connection with upper cushion layer 28, such as, but not limited to, soft core memory foam, gel-infused foam, and polyurethane foam.

Controller unit 38 is positioned between middle cushion layer 34 and lower cushion layer 40. In the illustrated embodiment, controller unit 38 is arranged as a layer of layer assembly 26. However, the arrangement of controller unit 38 is not limited thereto. Further, controller unit 38 may be embedded in cushion material to protect controller unit 38 from damage. In addition, it is contemplated that controller unit 38 may be located inside a housing unit.

The cushion material embedding controller unit 38 may include, but is not limited to, closed cell foam, rubber, and those materials described above in connection with upper and middle cushion layers 28 and 34. For example, such cushion materials of controller unit 38 may take the form of a foam material having a thickness in a range of about 0.25 inches to about 0.5 inches and a density in the range of about 4.0 lbs/ft$^3$ to about 20.0 lbs/ft$^3$.

Lower cushion layer 40 is located adjacent to bottom surface 22 of support pad 10. In the illustrated embodiment, lower cushion layer 40 is comprised of a foam material having a thickness in a range of about 0.125 inches to about 0.375 inches and a density in a range of about 1.5 lbs/ft$^3$ to about 2.5 lbs/ft$^3$. The foam material may take the form of a closed cell rubber material. However, lower cushion layer 40 may alternatively be formed of cushion materials as described above in connection with upper cushion layer 28.

It is noted that respective layer assemblies (not shown) of support pads 8 and 12 generally correspond with layer assembly 26 of support pad 10. Moreover, respective sensing devices 42 and 44 (see FIG. 5) of support pads 8 and 12 may be generally comprised of the same basic components as sensing device 32 of support pad 10. In addition, it will be appreciated that the inventive concepts described in terms of support pad 10 apply equally to support pads 8 and 12. Therefore, detailed descriptions of support pads 8 and 12 are omitted.

However, in the illustrated embodiment, support pads 8 and 12 have different dimensions than support pad 10. In this respect, support pads 8 and 12 are respectively dimensioned to support head and leg/foot regions of the patient.

Figure 5:
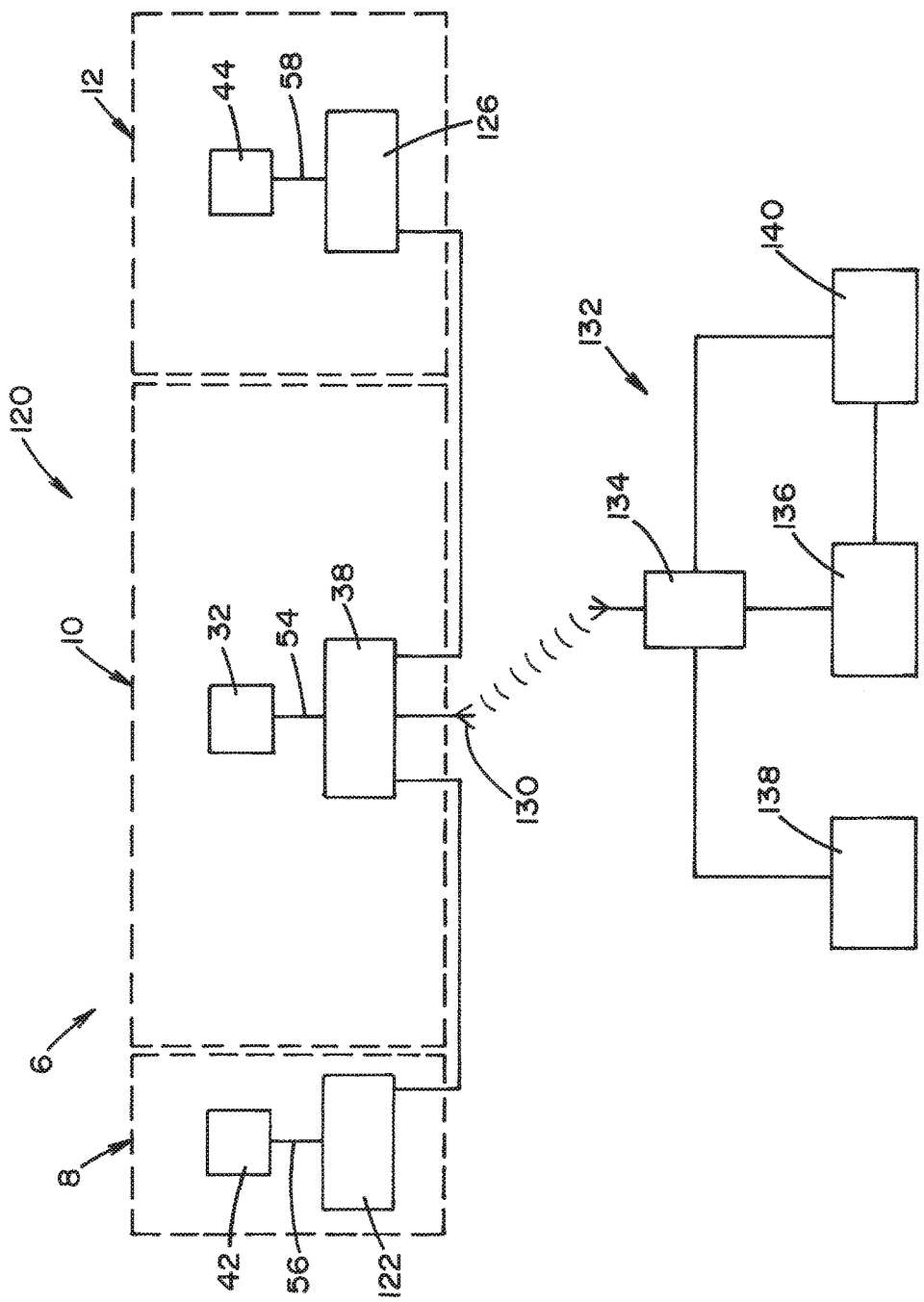
FIG. 5 is a schematic view of a monitoring system according to an embodiment of the present invention.

FIG. 5 shows a monitoring system 120 according to an embodiment of the present invention. Monitoring system 120 is generally comprised of a data acquisition system 132, at least one wireless communication module 130, respective sensing devices 42, 32, and 44 of support pads 8, 10, and 12, and respective controller units 122, 38, and 126 of support pads 8, 10, and 12.

In the illustrated embodiment, controller units 122, 38, and 126 are respectively electrically connected to sensing devices 42, 32, and 44 via respective communication interfaces 56, 54, and 58. Controller units 122, 38, and 126 receive respective signals from sensing devices 42, 32, and 44 indicative of pressure data sensed by sensing elements 52. In the illustrated embodiment, controller units 122 and 126 are further configured to relay respective pressure data received from sensing devices 42 and 44 to controller unit 38. The connections between controller units 122, 38, and 126 may be wired or wireless connections.

In the illustrated embodiment, controller unit 38 aggregates the pressure data originally acquired by sensing devices 42, 32, and 44 and communicates with data acquisition system 132 via wireless communication module 130. Controller unit 38 sends the aggregated data to data acquisition system 132 for storage and display of the aggregated data. It will be appreciated that wireless communication module 130 uses wireless communication protocols well known to those skilled in the art.

In the illustrated embodiment, controller unit 38 serves as a master controller, while controller units 122 and 126 serve as slave controllers. In this respect, controller unit 38 communicates with controller units 122 and 126, and with data acquisition system 132. However, the embodiments described herein are not limited thereto. Further, it will also be appreciated that other suitable arrangements for controller units 122, 38, and 126 may be implemented and will be apparent to those of ordinary skill in the art. For example, controllers 122 and 126 may send data collected from respective sensing devices 42 and 44 directly to data acquisition system 132 via wired or wireless means.

In addition, wireless communication module 130, respective sensing devices 42, 32, and 44 of support pads 8, 10, and 12, and respective controller units 122, 38, and 126 of support pads 8, 10, and 12 may receive power through surgical table 2 or any number of means known to one having ordinary skill in the art.

In the illustrated embodiment, data acquisition system 132 is generally comprised of a processing unit 134, an input unit 136, a data storage unit 138, and a display unit 140. Processing unit 134 receives the aggregated data from controller unit 38 and processes the data for storage in data storage unit 138 and/or for display by display unit 140. Input unit 136 is used to request data from data storage unit 138 to be retrieved for processing by processing unit 134 and display by display unit 140.

Manifestations of data acquisition system 132 may be implemented and will be apparent to those of ordinary skill in the art. For example, it will be readily appreciated that data acquisition system 132 may be contained within a personal computing device or distributed over a plurality of computing devices in multiple locations.

Data acquisition system 132 may advantageously employ any combination of computing devices, user inputs, displays, notification devices, storage servers, and networking components known to one having ordinary skill in the art. Input unit 136 may include, but is not limited to, a keyboard, a mouse controller, and a touch-screen. Display unit 140 may include, but is not limited to, a video display, a projector, and a printer. Devices corresponding with input unit 136 and display unit 140 are well known to the ordinary skilled artisan. It will be further appreciated that the processed data may be manifested in the form of pressure maps, pressure ulcer risk maps, graphs, or statistics, or any combination thereof.

FIG. 6 shows a cross-sectional side view illustrating an example of support pad 10 according to an embodiment of the present invention to which a distributed load is applied. Patient 150 is illustrated in FIG. 6 as applying a load to support pad 10 that is distributed, i.e., generally uniform, across an area of support pad 10. It is noted that, for the purposes of this discussion, a distributed load may be caused by areas of patient 150 that are positioned flat on support pad 10. In the illustrated embodiment, an area of support pad 10 on which the distributed load is applied generally corresponds to an area of load redistribution within support pad 10.

In FIG. 6, the load applied by patient 150 is generally distributed across top surface 20. It is assumed that cover 24 and upper cushion layer 28 provide good load transmission, thereby resulting in substantially direct transmission of the load through cover 24 and upper cushion layer 28 to sensing device 32. As a result, interface pressure sensed by sensing elements 52 is substantially equivalent to the load applied by patient 150 to support pad 10. Thus, pressure created by application of a distributed load of patient 150 to support pad 10 may be accurately measured by sensing device 32 with minimal or no increases in interface pressure.

FIG. 7 shows a cross-sectional side view illustrating an example of support pad 10 according to an embodiment of the present invention to which an acute load is provided. Patient 150 is illustrated in FIG. 7 as applying a load to support pad 10 that is acute, i.e., generally concentrated in a small area of support pad 10. An acute load may be caused by bony prominences of patient 150 that are positioned on support pad 10. Examples of bony prominences include, but are not limited to, areas of a pelvis of patient 150 or a heel of patient 150.

In FIG. 7, the illustrated bony prominence of patient 150 applies a load to the top surface 20 of support pad 10. It is assumed that cover 24 and upper cushion layer 28 provide good load redistribution, thereby resulting in substantially indirect transmission of certain portions of the load through cover 24 and upper cushion layer 28 to sensing device 32. Portions of the load applied by the bony prominence of patient 150 create tangential shear forces. These tangential shear forces are created by the bony prominence around an area of top surface 20 at which the bony prominence is supported. The created tangential shear forces are subsequently transmitted through cover 24 and upper cushion layer 28.

Expandable portions 101, tab portions 98, and openings 103 allow substrate 50 to stretch in response to the concentrated load that is directly transmitted through cover 24 and upper cushion layer 28. Thus, substrate 50 has a reduced resistance to loads applied to top surface 20 of support pad 10. The substrate 50 is further able to transmit corresponding pressure from bottom surface 30 of upper cushion layer 28 to top surface 36 of middle cushion layer 34. This allows bottom surface 30 of upper cushion layer 28 and top surface 36 of middle cushion layer 34 to conform to the stretched substrate 50, thereby reducing interface pressure at top surface 20 of support pad 10. This also allows cover 24 and upper cushion layer 28 to envelope the bony prominence of patient 150.

As substrate 50 is stretched in accordance with the load applied by the bony prominence, the tangential shear forces created by the bony prominence are transmitted through cover 24 and upper cushion layer 28 in directions that are increasingly more normal and direct to sensing device 32. As a result, load exposure to corresponding areas of sensing device 32 is increased and sensing accuracy of sensing device 32 is improved. Further, the resistance of substrate 50 to pressure is reduced. As a result, increases in the interface pressure at top surface 20 of support pad 10 are minimized or avoided.

While the present invention is particularly applicable for sensing pressure from within support pad 10 and is described with reference thereto, it will be appreciated from a further reading of the present disclosure that the present invention finds advantageous application in sensing other parameters from within support pad 10, such as, but not limited to, temperature. For example, temperature sensing elements could be used in place of pressure sensing elements 52 to sense a temperature of upper cushion layer 28.

Further, improved sensing accuracy of sensing device 32 may be achieved by other means in addition to the ability of substrate 50 to stretch. For example, sensing accuracy of sensing device 32 may additionally be improved by minimizing the thickness of upper cushion layer 28, which may improve direct transmission of the loads to sensing device 32.

In addition, while the present invention is particularly applicable for sensing with sensing elements 52 positioned in support pad 10, it will be appreciated from a further reading of the present disclosure that the present invention finds advantageous application in providing other functions with electronic elements positioned in support pad 10. These functions may include, but are not limited to, heating with heating elements positioned in support pad 10 and excitation with excitation elements positioned in support pad 10. For example, pressure sensing elements 52 may be replaced with heating elements to heat support pad 10.

The foregoing description provides example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A support pad, comprising:
   a first cushion layer;
   a second cushion layer; and
   a sensing device positioned between the first and second cushion layers, the sensing device comprising:
      a plurality of sensing elements; and
      a substrate including:
         a plurality of row and column sections, each of the column sections comprising one or more expandable portions biased in a contracted position, each expandable portion being configured to move between the contracted position and an expanded position in response to pressure being applied thereto;
         a plurality of tab portions, said sensing elements being respectively located on the tab portions; and
         a plurality of openings defined by the row sections, the column sections, and the tab portions, said tab portions being moveable within said openings,
   wherein each of said tab portions has a fixed end attached to one of the row sections and a free end extending from the one of the row sections into a corresponding one of the openings.

2. The support pad of claim 1, wherein the substrate further comprises a plurality of conductive trace lines formed on the row and column sections for electrically connecting the sensing elements.

3. The support pad of claim 2, wherein the conductive trace lines are moveable in accordance with the expandable portions.

4. The support pad of claim 1, wherein said first cushion layer is comprised of a foam material.

5. The support pad of claim 4, wherein said foam material of said first cushion layer has a density in a range of 2.8 lbs/ft$^3$ to 5.0 lbs/ft$^3$.

6. The support pad of claim 4, wherein said first cushion layer has a thickness in a range of 0.125 inches to 0.75 inches.

7. The support pad of claim 1, wherein said second cushion layer is comprised of a foam material.

8. The support pad of claim 7, wherein said foam material of said second cushion layer has a density in a range of 2.5 lbs/ft$^3$ to 4.0 lbs/ft$^3$.

9. The support pad of claim 7, wherein said second cushion layer has a thickness in a range of 1.0 inch to 4.0 inches.

10. The support pad of claim 1, wherein the pressure applied to the expandable portions is created by a load applied to the first cushion layer,
wherein said sensing elements are configured to sense the pressure applied to the expandable portions, and
wherein the load applied to the first cushion layer is transmitted through the first cushion layer to the sensing elements.

11. The support pad of claim 10, wherein the expandable portions expand in response to the load applied to the first cushion layer.

12. The support pad of claim 10, wherein the tab portions move in response to the load applied to the first cushion layer.

13. The support pad of claim 1, further comprising a cover that surrounds the first cushion layer, the second cushion layer, and the sensing device.

14. The support pad of claim 1, further comprising a controller unit and a third cushion layer, said controller unit being located between the second and third cushion layers.

15. The support pad of claim 14, wherein the sensing elements are configured to sense the pressure applied to the expandable portions, and
wherein said controller unit is electrically connected to the sensing device to receive signals from the sensing device indicative of the pressure applied to the expandable portions that is sensed by the sensing elements.

16. The support pad of claim 15, wherein said controller unit communicates with a data acquisition system for storing and displaying data acquired by the sensing device.

17. The support pad of claim 1, wherein the pressure applied to the expandable portions is applied by a bottom surface of the first cushion layer, and
wherein the substrate is configured to transmit the pressure applied to the expandable portions by the bottom surface of the first cushion layer to a top surface of the second cushion layer.

18. The support pad of claim 1, wherein the row and column sections are disposed between the tab portions.

19. A support pad assembly, comprising:
a first support pad, comprising:
a first cushion layer;
a second cushion layer; and
a sensing device positioned between the first and second cushion layers, the sensing device comprising:
a plurality of sensing elements; and
a substrate including:
a plurality of row and column sections, each of the column sections comprising one or more expandable portions biased in a contracted position, each expandable portion being configured to move between the contracted position and an expanded position in response to pressure being applied thereto;
a plurality of tab portions, said sensing elements being respectively located on the tab portions; and
a plurality of openings defined by the row sections, the column sections, and the tab portions, said tab portions being moveable within said openings,
wherein each of said tab portions has a fixed end attached to one of the row sections and a free end extending from the one of the row sections into a corresponding one of the openings.

20. The support pad assembly of claim 19, further comprising a second support pad electrically connected to the first support pad, the second support pad comprising:
a first cushion layer;
a second cushion layer; and
a sensing device positioned between the first and second cushion layers of the second support pad, the sensing device of the second support pad comprising:
a plurality of sensing elements; and
a substrate including:
a plurality of row and column sections, each of the column sections comprising one or more expandable portions biased in a contracted position, each expandable portion of the second support pad being configured to move between the contracted position and an expanded position in response to the pressure applied to the expandable portions of the first support pad;
a plurality of tab portions, said sensing elements of the second support pad being respectively located on the tab portions of the second support pad; and
a plurality of openings defined by the row sections of the second support pad, the column sections of the second support pad, and the tab portions of the second support pad, said tab portions of the second support pad being moveable within said openings of the second support pad,
wherein each of said tab portions of said second support pad has a fixed end attached to one of the row sections of the second support pad and a free end extending from the one of the row sections of the second support pad into a corresponding one of the openings of the second support pad.

* * * * *